US011969497B2

(12) United States Patent
Seguin

(10) Patent No.: US 11,969,497 B2
(45) Date of Patent: Apr. 30, 2024

(54) **METHOD FOR PRODUCING AN *ENTADA* SEED EXTRACT ENRICHED WITH METABOLITES OF INTEREST, EXTRACT PRODUCED BY SUCH A METHOD, AND COSMETIC AND DERMOCOSMETIC APPLICATIONS OF SUCH AN EXTRACT**

(71) Applicant: EXSYMOL, Monaco (MC)

(72) Inventor: Marie-Christine Seguin, Monaco (MC)

(73) Assignee: EXSYMOL, Monaco (MC)

( * ) Notice: Subject to any disclaimer, the term of this patent is extended or adjusted under 35 U.S.C. 154(b) by 813 days.

(21) Appl. No.: 17/046,638

(22) PCT Filed: Apr. 11, 2019

(86) PCT No.: PCT/EP2019/059298
§ 371 (c)(1),
(2) Date: Oct. 9, 2020

(87) PCT Pub. No.: WO2019/197548
PCT Pub. Date: Oct. 17, 2019

(65) Prior Publication Data
US 2021/0106515 A1 Apr. 15, 2021

(30) Foreign Application Priority Data
Apr. 12, 2018 (FR) .................................. 1853216

(51) Int. Cl.
| *A61K 8/9789* | (2017.01) |
| *A61K 8/46* | (2006.01) |
| *A61K 31/16* | (2006.01) |
| *A61K 36/48* | (2006.01) |
| *A61Q 19/08* | (2006.01) |

(52) U.S. Cl.
CPC .............. *A61K 8/9789* (2017.08); *A61K 8/46* (2013.01); *A61K 31/16* (2013.01); *A61K 36/48* (2013.01); *A61Q 19/08* (2013.01); *A61K 2236/19* (2013.01)

(58) Field of Classification Search
CPC ........ A61K 8/9789; A61K 8/46; A61K 31/16; A61K 36/48; A61K 2236/19; A61Q 19/08
See application file for complete search history.

(56) References Cited

U.S. PATENT DOCUMENTS

| 3,641,243 | A | 2/1972 | Liu |
| 7,815,948 | B2 | 10/2010 | Paufique |
| 9,815,783 | B2 | 11/2017 | Seguin |
| 2008/0038388 | A1 | 2/2008 | Paufique |
| 2009/0098617 | A1 | 4/2009 | Burke et al. |
| 2011/0129453 | A1 | 6/2011 | Harripersad |
| 2016/0303033 | A1 | 10/2016 | Beyer et al. |
| 2016/0362364 | A1* | 12/2016 | Seguin .................... A61K 8/36 |

FOREIGN PATENT DOCUMENTS

| CN | 106031498 | 10/2016 |
| EP | 3103436 | 12/2016 |
| FR | 2832418 | 5/2003 |
| FR | 2874503 | 3/2006 |
| WO | 9510530 | 4/1995 |
| WO | 2014165490 | 10/2014 |

OTHER PUBLICATIONS

Sufian, Md. Abu et al., "Biological investigation of *Entada rheedii* Spreng. and isolation of entadamide a from its seed," Int. Res. J. Pharm., 2015, 6(7), pp. 411-414.
Barua, A. K. et al., "Phaseoloidin, a homogentisic acid glucoside from *Entada phaseoloides*," Phytochemistry, 1988, vol. 27, No. 10, pp. 3259-3261.
Barua, C. C. et al., "An Overview of *Entada phaseoloides*: Current Research and Future Prospects," Journal of Pharmacy and Pharmacology, 2014, 2, pp. 1-18.
Barua, C. C. et al., "Effect of supplementation of *Entada phaseoloides* seed powder on growth performance, carcass characteristics and haemato—biochemical parameters along with its effect on expression of HSP70 in broiler chicken," Int. J. Res. Biosciences, 2015, 4(4), pp. 88-97.
Barua, C. C. et al., Phytochemicals, in vitro antioxidant activity and proximate composition of seeds of *Entada phaseoloides* Linn. Merrill. Int. J. Pharm. Bio. Sci., Jul. 2015, 6(3) pp. 366-376.
Consden, R. et al., "Observations on the Oxidation of Homogentisic Acid in Urine," Biochem J., 1951, vol. 50, pp. 274-278.
Dawane, J. S. et al., "Experimental evaluation of anti-inflammatory effect of topical application of *Entada phaseoloides* seeds as paste and ointment," North American Journal of Medical Sciences, Nov. 2011, vol. 3, No. 11, pp. 513-517.
Deepa, C. et al., "Proven Activities of *Entada phaseoloides* (L.) Merr.," Int. J. Curr. Res. Biosci. Plant Biol., 2017, 4(4), pp. 92-99.
Fujita, A. et al., "Conversion of Isoflavone Glucosides to Aglycones by Partially Purified β-Glucosidases from Microbial and Vegetable Sources," Appl. Biochem. Biotechnol., 2015, vol. 176, pp. 1659-1672.
Ikegami, F. et al., "Entadamide A, a new sulfur-containing amide from *Entada phaseoloides* seeds," Chem. Pharm. Bull., 1985, vol. 33, pp. 5153-5154.
Ikegami, F. et al., "Entadamide B, a second new sulphur-containing amide from *Entada phaseoloides*," Phytochem., 1987, vol. 26, No. 5, pp. 1525-1526.
Ikegami, F. et al., "Synthesis of Entadamide A and Entadamide B Isolated from *Entada phaseoloides* and Their Inhibitory Effects on 5-Lipoxygenase," Chem. Pharm. Bull., 1989, 37(7), pp. 1932-1933.
Iwamoto, Y. et al., "Entadosides A-D, triterpene saponins and a glucoside of the sulphur-containing amide from the kernel nuts of *Entada phaseoloides* (L.) Merrill," J. Nat. Med., 2012, 66, pp. 321-328.
Kren, V., "Glycoside vs. Aglycon: The Role of Glycosidic Residue in Biological Activity," Glycoscience, 2008, pp. 2589-2644.
Muniglia, L. et al., "Green Chemistry and Sustainable Technology," Chapter 8—Enzymatic Aqueous Extraction (EAE), 2014, pp. 167-204.

(Continued)

*Primary Examiner* — Shane Fang
(74) *Attorney, Agent, or Firm* — HSML P.C.

(57) ABSTRACT

The invention relates to a method for producing an extract of seeds of the *Entada* genus by selective hydrolysis of the metabolites accumulated in the seeds. The invention also relates to the extract produced using such a method, to a composition comprising such an extract, and to the cosmetic and dermocosmetic applications of such an extract.

28 Claims, No Drawings

(56) References Cited

OTHER PUBLICATIONS

Ohashi, H. et al., "*Entada* (*Leguminosae* subfam. *Mimosoideae*) of Taiwan," Taiwania, 2010, 55(1), pp. 43-53.

Shodhganga et al., Chapter 4—*Entada phaseoloides* (Linn.) Merrill., 2005, pp. 122-148, URL: shodhganga.inflibnet.ac.in/bitstream/10603/42603/9/09_chapter 4.pdf.

Singh, O. et al., "Phenolic acid glucosides from the seeds of *Entada phaseoloides* Merill," Journal of Asian Natural Products Research, Aug. 2011, vol. 13, No. 8, pp. 682-687.

Sofowora, A. et al., "The role and place of medicinal plants in the strategies for disease prevention," Afr. J. Tradit. Complement Altern. Med., 2013, 10(5), pp. 210-229.

Sripuan, T. et al., Proceedings of the twenty-four congress on Science and Technology of Thailand, Bangkok, Program and abstracts, 1998, ISBN 974-86505-5-3, pp. 638-639.

Sugimoto, S. et al., "Biological activity of *Entada phaseoloides* and *Entada rheedei*," J. Natur. Medicines, 2018, 72, pp. 12-19.

Wang, J. et al., "A comparison of acidic and enzymatic hydrolysis of rutin," Afr. J. Biotechnol., Feb. 21, 2011, vol. 10(8), pp. 1460-1466.

Xiong, H., "Sulfur-containing amides from *Entada phaseoloides*," Acta Pharmaceutica Sinica, 2010, 45 (5), pp. 624-626.

International Search Report and Written Opinion issued for International Patent Application No. PCT/EP2019/059298, dated Jun. 3, 2019, 14 pages including English translation of Search Report.

Sugimoto, S. et al., "Medicinal Plants of Thailand. I Structures of Rheedeiosides A-D and cis-Entadamide A β-D-Glucopyranoside from the Seed Kernels of *Entada rheedei*" Chem. Pharm. Bull., vol. 59, No. 4, 2011, pp. 466-471.

Koné, W. M. et al., "Traditional medicine in North Cote-d'Ivoire: screening of 50 medicinal plants for antibacterial activity," Journal of Ethnopharmacology, 93, 2004, pp. 43-49.

Inngjerdingen, K. et al., "An ethnopharmacological survey of plants used for wound healing in Dogonland, Mali, West Africa," Journal of Ethnopharmacology, 92, 2004, pp. 233-244.

Search Report issued for French Patent Application No. 1853216, dated Nov. 29, 2018, 3 pages.

\* cited by examiner

METHOD FOR PRODUCING AN *ENTADA* SEED EXTRACT ENRICHED WITH METABOLITES OF INTEREST, EXTRACT PRODUCED BY SUCH A METHOD, AND COSMETIC AND DERMOCOSMETIC APPLICATIONS OF SUCH AN EXTRACT

The present invention concerns a process for obtaining an extract obtained from a plant material and enriched in metabolites of interest, the extracts resulting from such a process and the compositions comprising such extracts, as well as their cosmetic and dermocosmetic applications.

According to the World Health Organization, plants qualified as "medicinal plants" for their beneficial properties for human health have been used since immemorial times in traditional medicine, particularly among weakly industrialized societies for which access to modern synthetic drugs remains expensive (Sofowora A. et al., Afr. J. Tradit. Alternate supplement. Med., 2013, vol. 10, pp. 210-229).

One of them, the species *Entada phaseoloides* which belongs to the genus "*Entada*" and more broadly to the botanical family of Fabaceae, has thus long been used in unconventional Ayurvedic, Chinese, or even tribal medicines (Deepa C. et al., Int. J. Curr. Res. Biosci. Plant Biol., 2017, vol. 4, pp. 92-99). Its distribution is rather cosmopolitan since the plant primarily developed in hot tropical zones such as the coastal forests of countries bordering the Indian Ocean: Madagascar, South Africa, India, Australia, etc. (Deepa C. et al., Int. J. Curr. Res. Biosci. Plant Biol., 2017, vol. 4, pp. 92-99). It is also found in Asia such in the central and eastern chain of the Himalayas and up to an altitude of 1300 meters (Singh O. et al., J. Asian Natur. Products Res., 2011, vol. 13, pp. 682-68'7), or even in China precisely under the name "*Entada phaseoloides* (L.) Merrill" (Xiong H. et al., Acta Pharmaceutica Sinica, 2010, vol. 45, pp. 624-626 and references cited). The morphology of the plant is the one of a climbing liana, carrying large pods after its inflorescence that can reach up to 2 m long and 13 cm wide. Each pod contains between 10 and 20 seeds of red-brown color, with a very hard shell, and whose shape looks like the one of an objective lens up to 10 cm in diameter (Sugimoto S. et al., J. Natur. Medicines, 2018, vol. 72, pp. 12-19).

The medicinal virtues recognized in the plant taken as a whole with its main organs (stem, leaves and seeds) are numerous and extremely varied: analgesic, anti-inflammatory, antiarthritic, anti-diabetic, antioxidant, hepatoprotective, antimicrobial, antispasmodic, cough suppressant, astringent, etc. However, the pharmacological experiments and studies carried out to date have mainly been carried out on plant seeds (Deepa C. et al., Int. J. Curr. Res. Biosci. Plant Biol., 2017, vol. 4, pp. 92-99). It is true on the one hand that once their whitish flesh is simply crushed and ground, these seeds have a wide range of uses: remedy against jaundice, constipation, snakebites, constipation, but also an use as hair growth stimulant, aphrodisiac, emetic, deworming, etc. (Barua C. C. et al., Int. J. Res. Biosciences, 2015, vol. 4, pp. 88-9'7; Barua C. C. et al., J. Pharm. Pharmacol., 2014, vol. 2, pp. 1-18). On the other hand, the analysis of the phytochemical constituents of the seed of *Entada phaseoloides* reveals the accumulation and storage of several secondary metabolites of interest (Shodhganga et al., 2005, URL address: shodhganga.inflibnet.ac.in/bitstream/10603/42603/9/09_chapter 4.pdf). Above all, there are abundant saponins which, in plants in general, turn out to be oily glycosides of cyclic triterpenes or of steroids, and which, in the case of *Entada phaseoloides* after acid hydrolysis, release a crystalline sapogenin with entagenic acid, and the glucosides arabinose and xylose. Significant anti-inflammatory activity, coupled with anti-diabetic and hypolipidemic activities, is very especially attributed to the saponins of *Entada phaseoloides* seeds (Barua C. C. et al., J. Pharm. Pharmacol., 2014, vol. 2, pp. 1-18 and references cited). Next, the seeds of *Entada phaseoloides* contain a multitude of phenolic acids and other flavonoids, mainly in the form of glycoconjugates such as the entity "phaseoloidin" frequently mentioned in the literature on the plant and which, after characterization, turned out to be the 2-O-β-D-glucopyranoside derivative of homogentisic acid (Barua A. K., Phytochem., 1988, vol. 27, pp. 3259-3261). Such a wealth of phenolic compounds made these seeds, logically thereafter, a raw material of choice for obtaining powerful and nutritious natural antioxidants (Barua C. C. et al., Int. J. Pharm. Organic. Sci., 2015, vol. 6, pp. 366-3'76). Also and in an original way for this climbing plant, it has been evidenced the presence in these seeds of thioamide structures called "entadamides", isolated and characterized for the first time by Japanese academics in the mid-1980s (Ikegami F. et al., Chem. Pharm. Bull., 1985, vol. 33, pp. 5153-5154 & Phytochem., 1987, vol. 26, pp. 1525-1526). Precisely with the number of two structures identified in the seeds, these metabolites are called "entadamide A" and "entadamide B". They chemically correspond to the compounds "trans-N-(2-hydroxyethyl)-3-methylthio-propenamide" and "N-(2-hydroxyethyl)-3,3-bis(methylthio)-propenamide" Quickly after their characterization, both have been proposed as new anti-inflammatory drugs after the evidence of an inhibitory effect on lipoxygenase (Ikegami F. et al., Chem. Pharm. Bull., 1989, vol. 37, pp. 1932-1933).

When applied topically to the skin, the same anti-inflammatory advantage is also observed through two tested formulations, ointment and paste, containing the crushed pulp of *Entada phaseoloides* seeds. They have indeed displayed an efficacy at least equal to that of a well-known non-steroidal anti-inflammatory drug, diclofenac (Dawane J. S., N. Am. J. Med. Sci., 2011, vol. 3, pp. 513-517). Identically in terms of skin care but concerning more specifically the only entadamide A, it can also be pointed out the EP 3103436 patent application filed by the applicant where the compound "(E)-N-(2-hydroxyethyl)-3-methylthiopropenamide", namely a synthetic replica of entadamide A, displays in the illustrative tests of the invention a broad spectrum of protective activities against solar radiation. Entadamide A is thus logically claimed therein in a cosmetic or dermocosmetic composition intended for photoprotection. Again for this entadamide A molecule but also for an "entadamide A-glucoside", a very recent article underlines their inhibitory action on the production of melanin, similar to that of the reference compound in the matter, arbutin (Sugimoto S. et al., J. Nat. Med., 2018, vol. 72, pp. 12-19). Its authors even predict for all entadamide derivatives an advantageous prospective with the following conclusion: «entadamides derivatives can be expected to be used as a new type of cosmetic» (Sugimoto S. et al., J. Nat. Med., 2018, vol. 72, pp. 12-19), after taking into account their structure considered not very similar with the current "cosmetic drugs" available commercially.

Based on these observations and in response to a growing demand for the incorporation of innovative, safe and effective active ingredients of natural origin into cosmetic products, the interest of the applicant in entadamide derivatives rose further after its past patent application, but newly this time through the design of a plant extract from *Entada* seeds with the optimal content in such metabolites for cosmetic purposes.

For this plant, a limiting knowledge is that many of the metabolites accumulated in its seeds exist in a form mostly precursor and sometimes less biologically active, with their conjugation to one or more glycosides of specific configuration or conformation (Kren V., Glycoscience, 2008, pp. 2589-2644). These are thus β-D-glucopyranose and β-D-glucopyranosyl-(1→3)-β-D-glucopyranose for entadamide A (Xiong H. et al., Acta Pharmaceutica Sinica, 2010, vol. 45, pp. 624-626), β-D-glucopyranose for homogentisic acid (Barua A. K., Phytochem., 1988, vol. 27, pp. 3259-3261), or even N-acetylglucosamine found in triterpene saponins (Iwamoto Y. et al., J. Nat. Med., 2012, vol. 66, pp. 321-328). Another difficulty is the observation of an entadamide A in glycosylated form which is unstable in solution in water and which unfavorably evolves towards the formation of by-products with a poorly defined structure and therefore devoid of any cosmetic interest.

Accordingly taking into account the foregoing, the technical problem that intends to solve the present invention is to develop on an industrial scale a process for obtaining an extract of *Entada* seeds enriched in entadamide A, precisely an entadamide A in a free or aglycone form. Such a process will therefore involve a step of hydrolysis of the precursor glycoside, and the access ultimately to an extract which can be used directly in cosmetics, that is to say without any step of separation and therefore of purification.

The problem to be solved in the design of the targeted extract also lies in the need to avoid the concomitant hydrolysis of other constituents of the extract. Thus, the normally expected presence of homogentisic acid resulting from the simultaneous hydrolysis of its glucosylated precursor with phaseoloidin, must be particularly avoided. It is indeed well known that besides being skin and ocular irritant according to the classification criteria of the European regulation (EC) No 1272/2008, this acid-phenol easily oxidizes to quinones which polymerize and thus form pigments that are poorly soluble in water and of very dark color (Consden R. et al., Biochem J., 1951, vol. 50, pp. 274-2'78). An extract provided with homogentisic acid is therefore unstable over time and will tend to evolve spontaneously towards the formation of a colored precipitate, consequently making such an extract inconsistent with the requirements imposed by the cosmetic formulation. Another pitfall to be avoided is lastly the simultaneous hydrolysis of the saponins which will be present in the extract, because it would lead to the loss of their traditionally recognized biological activities, as well as to the formation of aglycone triterpene compounds therefore poorly soluble in water and therefore liable once again to lead to the emergence of a precipitate in the extract.

In order to achieve these objectives, the applicant originally turned to chemical hydrolysis techniques, then to realize that it was not possible to obtain the expected selectivity above-mentioned. The applicant then turned to enzymatic hydrolysis techniques, known to the man skilled in the art to be more selective (Wang J. et al., African J. Biotech., 2011, vol. 10, pp. 14160-1466). The use of endogenous hydrolases, in particular glycosidases whose the presence had been reported in certain plants of the Fabaceae family to which the species *Entada phaseoloides* belongs (Sripuan T. et al., 1998, Proceedings of the twenty-four congress on Science and Technology of Thailand, Bangkok, Program and abstracts, ISBN 974-86505-5-3, pp. 638-639), appeared to be an opportunity to solve the technical problem raised by the invention. On the one hand, it already makes it possible to avoid the addition of hydrolytic enzymes of an exogenous source which may subsequently be difficult to remove from the final extract. On the other hand, a recent literature has specifically reported on endogenous β-glucosidases in several plants cultivated for their seeds, and in particular on their ability to convert large amounts of glucoside isoflavones into aglucone isoflavones and ultimately to increase bioavailability of these for their use in food (Fujita A. et al., Appl. Biochem. Biotechnol., 2015, vol. 176, pp. 1659-16'72).

On this basis, the applicant has sought to take advantage of this endogenous enzymatic activity of seed plants, in order to achieve a selective hydrolysis in an original way. However the hydrolases of *Entada phaseoloides* seeds have initially proved to be intrinsically poorly selective. Subsequently in contrast, and this is the basis of the present invention, the applicant has discovered that a sequential extraction procedure according to an appropriate panel of operating conditions makes it possible to obtain a very highly selective enzymatic hydrolysis of the main glycoconjugated metabolites such as present in the seeds of *Entada phaseoloides*, with a selectivity objectified by hydrolysis kinetics differences dependent on the nature of the substrate.

In other words, the inventors of the present invention have evidenced that the hydrolysis of the β-D-glucopyranoside forms of entadamide A and of phaseoloidin by an endogenous β-glucosidase could no longer be concomitant contrary to the technical assumption, with newly the implementation of an enzymatic activation step and then a deactivation step under very precisely controlled conditions: solvent, concentration, temperature, pH and hydrolysis time. In particular according to these controlled conditions, the inventors of the present invention have discovered that the introduction of certain organic solvents into the hydrolysis medium at a precise stage of the process made it possible to quickly stop the enzymatic hydrolysis process by inactivating irreversibly endogenous glycosidases. By thus adjusting the respective sensitivity of the metabolites, it was finally possible to limit the hydrolysis to only the glycosides of entadamide A.

Regarding a state of the art capable of approaching the solution to the problem, the prior art first of all reveals a fairly abundant literature around the Enzymatic Aqueous Extraction known as "EAE" (Muniglia L. et al., Part of the "Green Chemistry and Sustainable Technology" book, 2014, pp. 167-204). This is mainly proposed for "green chemistry" purposes and in the case of a plant substrate, it is in no way based on in situ selective hydrolysis, that is to say during the extraction, of one of the compounds present in the plant. The present invention also differs from that which is the subject of international application WO 95/10530 and from its priority application relating to a process for producing a plant extract enriched in aglucone isoflavones from one or more beta-glucosidase enzymes so as to convert a majority of glucone isoflavones in aglucone isoflavones. Unlike the present invention, there is no report of a selective hydrolysis of one in particular of the glucone isoflavones present in the plant.

The first object of the present invention is therefore a process for producing an extract of seeds of the genus *Entada* enriched in entadamide A, comprising the following steps:
  (i) an activation phase of endogenous enzymes, preferably of a β-glucosidase, by dispersion of said seeds under mechanical stirring in a seed/water weight ratio of about 0.02 to about 2;

(ii) a phase of enzymatic hydrolysis of the dispersion obtained in step (i) by heat treatment at a temperature between about 25 and about 100° C. and for a time period of between about 2 minutes and about 12 hours, at a pH of between about 4 and about 8;

(iii) an inhibition phase of the enzymatic activity in the dispersion thermo-chemically obtained in step (ii), said phase successively comprising the following steps:
   a) the addition of an agent irreversibly inhibiting the activity of the endogenous enzymes in an inhibitory agent/water volume ratio of between about 0.1 and about 10;
   b) a heat treatment of the reaction medium obtained in step (iii/a) at a temperature of between about 25 and about 75° C. and for a time period of between about 2 minutes and about 12 hours;
   c) removal of the inhibitory agent referred to in step (iii/a) under reduced pressure in order to obtain an aqueous filtrate enriched in entadamide A and containing a native non-hydrolyzed phaseoloidin.

(iv) the addition of a cosmetically acceptable solvent to the aqueous filtrate obtained in step (iii/c), followed by a step of adjustment of the pH between about 3 and about 7.

By "extract of seeds of the genus *Entada* enriched in entadamide A" as obtained at the end of step (iv), it is necessary to understand above all and in the first place an extract which fulfills at least one of the following criteria:

an extract enriched in entadamide A in free form (aglucone) and no longer containing entadamide A glucone or containing only traces of entadamide A glucone not exceeding a weight content of 200 ppm (or 0.2 mg/g);

an extract enriched in entadamide A, in particular by comparison with an extract obtained according to an hydro-alcoholic-type traditional extraction which only allows the recovery of very small amounts of aglucone metabolite;

an extract comprising a weight content of between about 1 and about 5 mg/g of entadamide A, preferably a content of between about 2 and about 3 mg/g of entadamide A;

an extract comprising a weight content of between about 9 and about 85 mg/g of phaseoloidin, preferably a content of between approximately 30 and approximately 60 mg/g of phaseoloidin;

an extract in which the phaseoloidin/entadamide A weight ratio is between about 15 and about 25, preferably about 20;

an extract in which the entadamide A glucone/entadamide A weight ratio is less than 0.5, preferably less than 0.1;

an extract characterized by a conversion rate of entadamide A glucone to entadamide A of at least 90%, preferably of 99%;

an extract which has not undergone any separation step by chromatography.

In the second place, it is necessary to understand by "extract of seeds of the genus *Entada* enriched in entadamide A" an extract which fulfills at least one of the criteria hereafter:

an extract not containing homogentisic acid or containing only traces of homogentisic acid not exceeding a maximum content of a few tens of ppm, preferably 50 ppm (or 0.05 mg/g);

an extract comprising a weight content of between about 3 and about 40 mg/g of saponins, preferably a content of between approximately 10 and approximately 20 mg/g of saponins;

an extract containing an optimal amount of phaseoloidin with an extraction yield of phaseoloidin of at least 90%, preferably 100%.

According to a preferred embodiment of the invention, it is meant by "seeds of the genus *Entada*" according to the invention some whole or shelled, germinated or non-germinated seeds, beforehand crushed or ground, and possibly reduced to the state of powder. These seeds are obtained from one or more of the species *Entada phaseoloides, Entada rheedei, Entada parvifolia, Entada pursaetha, Entada scandes, Entada gigas* and *Entada africana* with regard to the similarity announced of their phytoconstituents (Deepa C. et al., Int. J. Curr. Res. Biosci. Plant Biol., 2017, vol. 4, pp. 92-99; Sugimoto S. et al., J. Natur. Medicines, 2018, vol. 72, pp. 12-19; Abu Sufian Md. et al., Int. Res. J. Pharm., 2015, vol. 6, pp. 411-414), of their synonymy or of their qualification as a "subspecies" (Ohashi H. et al., Taiwania, 2010, vol. 55, pp. 43-53). Advantageously, they are seeds derived from the species *Entada phaseoloides* or *Entada rheedei*. Very particularly, they are seeds from the species *Entada phaseoloides*.

According to a preferred embodiment of the invention, the seeds are shelled, crushed or ground, and optionally reduced to the state of powder.

According to a preferred embodiment of the invention, the seed/water weight ratio of step (i) is between about 0.1 and about 1, preferably about 0.2.

According to a preferred embodiment of the invention, the temperature in the heat treatment of step (ii) is between about 45 and about 60° C., preferably about 55° C.

According to a preferred embodiment of the invention, the duration of the heat treatment of step (ii) is between about 10 minutes and about 1 hour, preferably about 30 minutes.

According to a preferred embodiment of the invention, the pH is adjusted between about 4 and about 6 during the heat treatment of step (ii).

According to a preferred embodiment of the invention, the agent inhibiting the activity of the endogenous enzymes used in step (iii/a) is an organic solvent miscible with water, advantageously glucose-added water or an alcohol chosen from ethanol, methanol, propanol and its isomers, butanol and its isomers, pentanol, hexanol, and mixtures thereof. Advantageously, it is ethanol or methanol. Very particularly, it is ethanol.

According to a preferred embodiment of the invention, the inhibitory agent/water volume ratio of step (iii/a) is between about 0.5 and about 5, preferably about 1.

According to a preferred embodiment of the invention, the temperature in the heat treatment of step (iii/b) is between about 45 and about 60° C., preferably about 55° C.

According to a preferred embodiment of the invention, the duration of the heat treatment of step (iii/b) is between about 10 minutes and about 1 hour, preferably about 30 minutes.

According to a preferred embodiment of the invention, the cosmetically acceptable solvent used in step (iv) is a glycolic solvent, advantageously chosen from 1,3-propanediol, 1,2-propanediol (propylene glycol), methylpropanediol, phenoxypropanediol, 1,2-butanediol (butylene glycol), 1,3-butanediol, 1,4-butanediol, 2,3-butanediol, 1,2-hexanediol, 1,2-dihydroxyethane (ethylene glycol), diethylene glycol, dipropylene glycol, triethylene glycol, tripropylene glycol, diethoxy diglycol, pentylene glycol, hexylene glycol, 1,2-octanediol (caprylyl glycol), glycerin (glycerol), and mixtures thereof. Advantageously, it is 1,3-propanediol or 1,2-butanediol or glycerin. Very particularly, it is 1,3-propanediol.

According to a preferred embodiment of the invention, the adjustment pH of step (iv) is about 4.5.

As an illustrative example of the first object of the invention, an extract of seeds of the species *Entada phaseoloides* enriched in entadamide A is prepared according to a process comprising the following steps:
(i) activation of the endogenous β-glucosidase of 10 g of shelled and then ground seeds of *Entada phaseoloides* by placing them in suspension with mechanical stirring in 50 g of water;
(ii) enzymatic hydrolysis of the suspension at a temperature of 55° C. for 30 minutes;
(iii) addition of 50 ml of ethanol and reaction medium brought to a temperature of 55° C. for another 30 minutes, followed by filtration to obtain a clear filtrate;
(iv) 100 g of filtrate ("crude extract") obtained in step (iii) are added to 7.3 g of 1,3-propanediol, which, after evaporation under reduced pressure and introduction of 50 ml of water, new evaporation under reduced pressure, addition of a few drops of 6N HCl and adjustment with 24.3 g of water, yield a hydroglycolic extract called "extract of *Entada* seeds" in the formulation and tests 1 to 7 hereafter and containing under these conditions:

2.5 mg/g of entadamide A;
43 mg/g of phaseoloidin;
10 to 15 mg/g of saponins;
a phaseoloidin/entadamide A weight ratio of less than 20;
an entadamide A glucone/entadamide A weight ratio of less than 0.1;
a non-detectable amount of homogentisic acid, at least less than 50 ppm (or 0.05 mg/g);
a non-detectable amount of entadamide A glucone, at least less than 50 ppm (or 0.05 mg/g).

The present invention also relates to an extract of seeds of the genus *Entada* enriched in entadamide A which is obtainable by the process such as defined above.

Another object according to the invention is an extract of seeds of the genus *Entada* enriched in entadamide A obtainable by the process according to the invention, for its use in cosmetics or dermocosmetics since said extract has displayed a set of advantageous responses for the skin, illustrated by tests 1 to 7 below:
an ability to oppose the photo-induced isomerization of an endogenous photoprotective agent with trans-urocanic acid, consequently a capacity to limit the immunosuppressive effects of the ultra-violet B component of solar radiation (UV-B: λ 290-320 nm) [see test 1a below]. Regarding such a photo-inhibitory activity of the extract according to the invention with respect to the photo-induced isomerization of trans-urocanic acid to cis-urocanic acid, it should be noted, and it is another important aspect of the invention, the significant contribution, unknown to date to the knowledge of the applicant, of non-hydrolyzed phaseoloidin, greater than at least 25% in such photoprotective activity against UV-B radiation [see test 1b below];
a powerful antioxidant activity for said extract, which is of interest at the cutaneous level to oppose any oxidative stress generating free radicals or reactive species derived from oxygen ($O_2^{\circ-}$, $H_2O_2$, $OH^{\circ}$, etc). Such an effect was observed when said extract was assessed in the context of tests with ABTS (2,2-azinobis-(3-ethylbenzothiazoline-6-sulfonic acid) [see test 2a below] and with DPPH (1,1-diphenyl-2-picrylhydrazyl) [see test 2b below];
an ability to limit the photo-induced overproduction of a protein, i.e. galectin-7, such an effect on this protein marker constitutes another indication of the efficiency of the extract in effectively opposing the immunosuppression induced by UV-B [see test 3 below];
an ability to limit the release of pro-inflammatory cytokine mediators of IL-8 and TNF-alpha types induced by UV-B radiation, markers designated to study the inflammatory effects of UV-B [see tests 4 and 5 below];
an ability to fight effectively against other components of solar radiation, such as ultraviolet-A radiation (UV-A: λ 320-400 nm) or visible radiation (VIS: λ 400-700 nm), in particular against blue light (λ 380-470 nm) where said extract, due to its antioxidant properties, is able to oppose the overproduction of a matrix metalloproteinase, MMP-1, induced by blue light and which degrades the collagen [see test 6 below];
an ability to limit, on explants of human skin in culture, DNA damage induced by the combination of UV-B, UV-A and VIS radiations and expressed by the quantity of pyrimidine dimers ("CPDs") [see test 7 below];
an ability to protect the *Staphylococcus epidermidis* commensal bacterium from UVB-induced damage [see test 8 below].

For one of the above-mentioned tests (test 2), it should be noted the comparative values between the extract according to the present invention and a synthetic replica of entadamide A referred to in patent application EP 3103436 filed by the applicant.

According to a preferred embodiment of the invention, the cosmetic use of an extract of seeds of the genus *Entada* enriched in entadamide A obtainable by the process according to the invention relates to the prevention or the fight against the effects of solar radiation harmful to the skin, in particular against ultraviolet-B radiation (UV-B: λ 290-320 nm), whether to reinforce the effectiveness of photo-protective formulas applied topically or more generally to slow down photo-aging.

According to another preferred embodiment of the invention and due to the antioxidant properties of the extract according to the invention, the use of such an extract of seeds of the genus *Entada* enriched in entadamide A obtainable by the process according to the invention relates to the prevention or the fight against the cutaneous signs resulting from stress such as atmospheric pollution, contact with chemical xenobiotics or smoky atmospheres.

Another preferred embodiment of the invention relates to an extract of seeds of the genus *Entada* enriched in entadamide A obtainable by the process according to the invention, for its dermocosmetic use in the treatment of acne, seborrhea, rosacea or atopic dermatitis, due to its anti-inflammatory properties.

Another preferred embodiment of the invention is its cosmetic use in maintaining homeostasis of the microbiome at the surface of the skin, due to the photo-protective and anti-oxidant properties displayed by the extract of seeds of the genus *Entada* enriched in entadamide A obtainable by the process according to the invention.

Finally, another object of the invention relates to a composition for cosmetic or dermocosmetic use, comprising, as main active ingredient, an extract of seeds of the genus *Entada* enriched in entadamide A as defined above, in combination with one or more additives physiologically compatible with skin or appendages.

Advantageously, the amount of extract of seeds of the genus *Entada* enriched in entadamide A as defined above in the targeted compositions is between 1% and 10% by weight relative to the total weight of the composition, preferably between 1.5% and 5% by weight.

The compositions according to the invention are suitable for topical cutaneous administration, presented in all the forms normally used for such administration. By way of non-limiting information, compositions can be in the form of suspensions, lotions, creams, aqueous or hydroalcoholic gels, powders and various emulsions which may be optionally micro-emulsions or nanoemulsions, etc.

The compositions according to the invention may contain as physiologically acceptable additive at least one additive known by the skilled person and compatible in cosmetic or dermocosmetic areas, chosen among oils, waxes, silicone elastomers, surfactants, co-surfactants, thickeners and/or gellants, humectants, emollients, organic or inorganic filters, photostabilizing agents, preservatives with the exception of aldehyde donor preservatives, dyes, matifying agents, tensors, sequestering agents, perfumes, etc, and mixtures thereof.

The compositions according to the invention may further comprise one or more additional active agents, chosen, without this list being limiting, from deglycation agents, agents that increase the synthesis of collagen or elastin or prevent their degradation, agents that increase the synthesis of glycosaminoglycans or proteoglycans or prevent their degradation, agents that increase the cell proliferation, propigmenting agents, antioxidant or anti-radical or anti-pollution agents, moisturizing agents, draining or detoxifying agents, anti-inflammatory agents, desquamative agents, soothing and/or anti-irritating agents, agents that act on the microcirculation (anti-dark circles), agents reinforcing skin defense systems, agents favorable to the reinforcement of the barrier function, agents stimulating cell metabolism:cell growth, production of biomolecules useful for skin such as collagen, agents opposing the harmful effects of psychological stress, molecular chaperones, agents limiting the drawbacks associated with an overproduction of sebum, agents targeting certain skin pathologies such as atopic dermatitis, rosacea, healing disorders, and mixtures thereof.

Very particularly in the uses and compositions according to the invention, the extract of seeds of the genus *Entada* enriched in entadamide A capable of being obtained by the process according to the invention is an extract of shelled and ground seeds of *Entada phaseoloides*. Purely as an indication, the present invention is illustrated below by the following example of formulations of composition according to the invention containing an extract of seeds of the genus *Entada* enriched in the aforementioned entadamide A.

Formula a (Cream)—Topical Application: Photo-Aging (Mass Percentages)

| | |
|---|---|
| Entada phaseoloides seed extract | 2% |
| Hydrogenated polyisobutene | 7% |
| Isobutyl myristate | 3% |
| Cetyl palmitate | 7% |
| Ethylene glycol monostearate | 5% |
| Laurate sorbitan | 2% |
| Polysorbate 20 | 2% |
| Carbomer (acrylate/acrylamide copolymer & mineral oil) | 0.3% |
| Phenoxyethanol | 0.5% |
| Water | qsp 100% |

Formula B (Gel)—Topical Application: Anti-Pollution (Mass Percentages)

| | |
|---|---|
| Entada phaseoloides seed extract | 4% |
| Carbomer (acrylate/acrylamide copolymer & mineral oil) | 1.5% |
| Sodium benzoate | 0.2% |
| Sorbic acid | 1% |
| 1,3-butanediol | 10% |
| Glycerin | 5% |
| Sodium hydroxide | 0.13% |
| Phenoxyethanol | 0.9% |
| Water | qsp 100% |

The present invention is also illustrated below, purely as an indication, by the following tests mentioned above in the description of the invention (tests 1 to 7).

The experiments of tests 3 to 5 were all carried out on human epidermis reconstructed on D17, called "EHR" (supplier: Skinethic®), cultured in a maintenance medium then irradiated at a dose of 300 mJ/cm$^2$ (Waldmann® lamp) in the presence or absence of the *Entada* seed extract according to the invention. After 24 h of culture, the supernatants were harvested and the protein assays were then carried out according to the protocols below.

Test 1: Demonstration of the Ability of an Extract of *Entada phaseoloides* Seeds to Oppose the Photo-Induced Isomerization of Trans-Urocanic Acid Two series of experiments were performed, the first with a fixed dose UV-B radiation of 300 mJ/cm$^2$ (test 1a), the second with a varying dose of UV-B radiation (test 1b) and using as a control a synthetic replica of entadamide A, namely the compound "(E)-N-(2-hydroxyethyl)-3-methyl-propenamide" which is the subject of patent application EP 3103436.

Experimentally, the test was carried out in a 0.01 M citrate buffer of pH 5.5, the slightly acidic pH being more in relation to the acidity of the superficial skin layers in which the trans-urocanic acid marker is located. Thus, the solutions to be irradiated (20 mL), namely the control with or without the extract according to the invention, were placed in glass Petri dishes, uncovered, then subjected at room temperature to UV-B irradiation using a UV-B oven (LabOSI®). Aliquots (500 µL) were then sampled in HPLC vials to be immediately stored protected from light and at low temperature (+4/+8° C.), prior to analysis by HPLC assay. Chromatographic profiles were thus obtained, and the residual amount of trans-urocanic acid was determined.

The results obtained in the context of test 1a are collated in the following table 1a:

TABLE 1a

| Compound | % trans-urocanic acid (at 300 mJ/cm$^2$) | % of increase of trans-urocanic acid |
|---|---|---|
| Trans-urocanic acid (non-irradiated control) | 100 | N/A |
| Trans-urocanic acid (irradiated control) | 37 | N/A |
| Control (irradiated) + extract of Entada seeds at 2% | 53 | +43% |
| Control (irradiated) + extract of Entada seeds at 3% | 56 | +51% |
| Control (irradiated) + extract of Entada seeds at 5% | 64 | +73% |

The results in Table 1a above emphasize that the extract of *Entada* seeds according to the invention, at the lowest concentration tested, is effective in the prevention of photo-isomerization of the trans-urocanic acid into cis-urocanic acid.

Experimentally concerning test 1b, the study was carried out in an almost identical manner to test 1a above, with first checking that under the experimental conditions defined, trans-urocanic acid generated a significant amount of cis-urocanic acid which can be measured by HPLC analysis.

The irradiation dose was 64 and 128 mJ·cm$^{-2}$. The results obtained in the context of test 1b are collated in Table 1b below:

TABLE 1b

| Compound | % inhibition of trans -> cis isomerization of urocanic acid | |
|---|---|---|
| | 64 mJ/cm$^2$ | 128 mJ/cm$^2$ |
| Control: entadamide A (1 mM) | 34 | 40 |
| Extract of Entada seeds (entadamide A (1 mM) + phaseoloidin) | 54 | 59 |

The results of Table 1b above firstly underline that the extract of *Entada* seeds according to the invention is effective in the protection of trans-urocanic acid against UV-B irradiation, with a capacity to limit its photo-isomerization. Then, these results highlight the important contribution of phaseoloidin in the photoprotective power of the extract.

Test 2: Demonstration of the Antioxidant Activity of an Extract of *Entada phaseoloides* Seeds Two series of experiments were performed, the first with the test ABTS or acid 2,2-azinobis-(3-ethylbenzothiazoline-6-sulfonic acid (test 2a), the second with the test DPPH or 1,1-diphenyl-2-picrylhydrazyl (test 2b). Ascorbic acid was used as a reference antioxidant. Experimentally according to the test ABTS, a mother solution of oxidized ABTS salt (diammonium salt of 2,2'-azinobis(3-ethylbenzothiazoline-6-sulfonic acid) was obtained beforehand by mixing volume to volume 7 mM of diammonium salt of 2,2'-azinobis(3-ethylbenzothyazoline-6-sulfonic acid) with 2.45 mM potassium persulphate for 16 hours. This solution was then was diluted in water to obtain, under the test conditions, an absorbance of 0.5 at 734 nm. In each well of a 96-well microplate, were placed 100 µL of a solution of the extract according to the invention to be evaluated and 150 µL of oxidized ABTS solution. After 6 minutes, the absorbance was measured at 734 nm.

The results obtained are collated in Table 2a below:

TABLE 2a

| Compound | EC$_{50}$ |
|---|---|
| Entada extract | 74 mg/L (i.e. 9.6 µM equivalent phaseoloidin) |
| phaseoloidin | 8.3 µM |
| ascorbic acid | 24 µM |

Experimentally by the DPPH test in each well of a 96 well micro plate, were placed 100 µL of a solution of the active to be evaluated and 100 µL of an ethanol solution of 1,1-diphenyl-2-picrylhydrazyle (DPPH-Aldrich D913-2) at 200 µM. After 30 minutes, the absorbance was measured at 517 nm.

The results obtained are collated in Table 2b below:

TABLE 2b

| Compound | EC 50 |
|---|---|
| Entada extract | 0.84 mg/l (i.e. 109 µM equivalent phaseoloidin) |
| phaseoloidin | 540 µM |
| ascorbic acid | 25 µM |

The results are Tables 2a and 2b emphasize that phaseoloidin is a powerful antioxidant close to ascorbic acid, it confers to the extract an activity which can be used in the context of a cosmetic application.

Test 3: Demonstration of the Capacity of an Extract of *Entada phaseoloides* Seeds to Limit the Secretion of a Protein, Galectin-7

Experimentally, after irradiation and harvesting of the supernatants, the assay of galectin-7, an apoptotic protein, was carried out using a ELISA kit (human Galectin-7 R & D System DY13339, supplier: Biotechne). The anti-galectin-7 capture antibodies were first attached to the bottom of wells of a 96-well plate. Then, after washing and blocking, 100 µL of the different culture supernatants of the harvested EHRs were placed in the wells. Molecules of galectine-7 present in the samples thus specifically fixed to the capture antibodies and those that were not fixed were removed during a rinsing step. The secondary detection antibody (which carries biotinylated sites) was then added into the wells. After washing, streptavidin-HRP, a protein with a high affinity for biotin, was added and fixed onto the biotinylated sites of the secondary antibody. After a final rinsing step to remove the excess streptavidin-HRP, the peroxidase substrate was added and the reaction was quenched with a solution containing sulfuric acid after twenty minutes. The colorimetric intensity was measured by spectrophotometry at 450 nm.

The results obtained are collated in Table 3 below:

TABLE 3

| Compound | % of galectin-7 secreted | % of inhibition of galectin-7 secretion |
|---|---|---|
| Control (non-irradiated EHR) | 100 | N/A |
| Control (irradiated EHR) | 1084 | N/A |
| Control (irradiated EHR) + extract of Entada seeds at 2.5% | 301 | −72% |

The results of Table 3 underline that under a dose of UV-B radiation, the extract of *Entada* seeds according to the invention is capable of reducing by more than 70% the amount of galectin-7 secreted by reconstructed human epidermis.

Test 4: Demonstration of the Capacity of an Extract of *Entada phaseoloides* Seeds to Limit the Release of Pro-Inflammatory Mediators of the IL-8 Type Experimentally, after irradiating and harvesting the supernatants, the assay of cytokine IL-8, synonymous with an increase in inflammation under UV-B, was carried out using an ELISA kit of the "Human CXCL8/IL-8. Immunoassay D8000C" type (supplier: Biotechne). A technique identical to the assay of galectin-7 was used.

The results obtained are collated in Table 4 below:

TABLE 4

| Compound | % of IL-8 secreted | % of inhibition of IL-8 secretion |
|---|---|---|
| Control (non-irradiated EHR) | 100 | N/A |
| Control (irradiated EHR) | 1213 | N/A |
| Control (irradiated EHR) + extract of Entada seeds at 1.5% | 221 | −80% |

The results of Table 4 underline that under a dose of UV-B radiation, the extract of *Entada* seeds according to the invention is capable of greatly reducing the secretion of IL-8.

Test 5: Demonstration of the Capacity of an Extract of *Entada phaseoloides* Seeds to Limit the Release of Inflammatory Mediators (TNF-Alpha)

Experimentally, after irradiating and harvesting the supernatants, the assay of cytokine TNF-alpha, a pro-inflammatory cytokine playing an important role in immune reactions and having a preponderant place in photo-induced immunosuppression, was carried out using a ELISA kit of the "Quantikine Human TNF-alpha Immunoassay DTA00C" type (supplier: Biotechne), and with the same analysis technique as for galectin-7 and IL-8.

The results obtained are collated in Table 5 below:

TABLE 5

| Compound | % of TNF-alpha secreted | % of inhibition of TNF-alpha secretion |
|---|---|---|
| Control (non-irradiated EHR) | 100 | N/A |
| Control (irradiated EHR) | 229 | N/A |
| Control (irradiated EHR) + extract of Entada seeds at 1.5% | 165 | −28% |

The results of Table 5 underline that under a dose of UV-B radiation, the extract of *Entada* seeds according to the invention is capable of reducing the secretion of TNF-alpha.

Test 6: Demonstration of the Ability of an Extract of *Entada phaseoloides* Seeds to Limit the Overexpression of the MMP-1 Metalloproteinase Induced by Blue Light Primary human fibroblasts ("NHDF") were isolated from a mammoplasty from a 17 year old patient. The NHDFs were cultured in DMEM medium supplemented with 4.5 g/l of glucose and 10% of FCS. They were maintained in an atmosphere at 37° C. and 10% $CO_2$. On D-3, the fibroblasts were inoculated in 24-well plates at a rate of 15,000 cells/$cm^2$. On D-1, the NHDFs were incubated at 37° C. and 10% $CO_2$ for 24 h with the extract of *Entada* seeds according to the invention. On D0, the treatments were renewed and the cells were exposed to a dose of 30 J/$cm^2$ of blue light (lamp Waldmann®, with fluocompact bulb LIGHTTECH LTC 36W/2G11 CL 380-470 nm). After irradiation, the cells were reincubated at 37° C. and 10% $CO_2$ for an additional 24 h and the culture supernatants were harvested in order to perform an ELISA assay of the MMP-1 metalloproteinase (Abcam kit, ab100603). The results obtained were normalized with respect to the quantity of cells per condition and subjected to statistical analysis in triplicate. N-acetyl-cysteine ("NAC") was used as a standard antioxidant.

The results obtained are collated in Table 6 below:

TABLE 6

| Compound | % of MMP-1 secreted | % of inhibition of MMP-1 secretion |
|---|---|---|
| Control (non-irradiated NHDF) | 100 | N/A |
| Control (irradiated NHDF) | 214 | N/A |
| Control (irradiated NHDF) + N-acetyl-L-cysteine (NAC) 5 mM | 61 | −71% |
| Control (irradiated NHDF) + extract of Entada seeds at 0.05% | 46 | −79% |

The results of Table 6 underline an efficacy of the extract of *Entada* seeds according to the invention comparable to that of N-acetyl-cysteine.

Test 7: Demonstration of the Capacity of an Extract of *Entada phaseoloides* Seeds to Limit, on Explants of Human Skin in Culture, the DNA Damage Induced by the Combination of UV-B, UV-A and VIS Radiation.

The demonstration was carried out using the in situ immunostaining technique on explants of human skin in culture (human skin obtained from a scalp of the temporal area of Caucasian women aged 42 and 56 years), after making squares of skin of about 1 $cm^2$ with a scalpel. The culture of the explants consisted in placing them in a "DMEM" growth medium containing 4.5 g/L of glucose, supplemented with antibiotics (penicillin-streptomycin-amphotericin) and topically treated with the extract of *Entada* seeds according to the invention at a concentration of 2.5%, and this for 48 hours at 37° C. and 5% $CO_2$.

After application of the extract, the explants were irradiated in a solar simulator (SUNTEST CPS+). After irradiation, the treatment was renewed immediately and the explants were cultured for 24 hours.

At the end of the culture time, the explants were frozen and then 5 μm thick cross-sections of each explant were obtained using a cryotome. Immunostaining of the pyrimidine dimers ("CPDs") was performed using specific antibodies. Each slice or section of skin was then observed using an epifluorescence microscope, with three photographs taken at ×20 magnification for each section, then a measurement of the overall amount of fluorescence of the labelling was carried out using an image analysis software. The results of each condition were compared to the control condition.

The results obtained are collated in Table 7 below:

TABLE 7

| Compound | Global amount of fluorescence (UA) | % of decrease of CPDs |
|---|---|---|
| Control (non-irradiated explants) | 921116 | N/A |
| Control (irradiated explants) | 4987094 | N/A |
| Control (irradiated explants) + extract of Entada seeds at 2.5% | 1915520 | −61% |

The results of Table 7 underline that under a dose of solar radiation, the extract of *Entada* seeds according to the invention is capable of significantly limiting the formation of pyrimidine dimers (CPDs) induced by solar radiation.

Test 8: Skin Microbiota Protection Test Showing the Ability of an Extract of *Entada Phaseoloides* Seeds to Protect the Commensal Bacteria *Staphylococcus epidermidis* from UVB-Induced Damage Experimentally, the tests were carried out in tubo. The bacterial strain *Staphylococcus epidermidis* (Alliance bioexpertise ATCC 12228) was subjected to UV-B irradiation of 100, 150 and 300 mJ/cm² (Waldmann lamp, irradiance 0.73 mW/cm²), in the presence or not of the extract of interest at 1%, 1.5% and 2.5%.

100 μL of suspension were then placed on TSA agar (Biomërieux, ref 43011) and then incubated at 37° C. under aerobic culture conditions. A manual counting of bacterial colonies was carried out 24 hours later. The results are expressed as a percentage of CFU (Colony Forming Units) relative to the non-irradiated control, representative of bacterial viability. The results are presented in Table 8 below:

TABLE 8

| Compound | % CFU (bacterial viability) | | |
|---|---|---|---|
| | Non-irradiated | 100 mJ/cm² | 150 mJ/cm² |
| Untreated *S. epidermidis* | 100 | 77 | 49 |
| *S. epidermidis* + Entada extract at 1% | 99 | 89 (+16%) | 73 (+49%) |
| *S. epidermidis* + Entada extract at 1.5% | 98 | 95 (+23%) | 89 (+82%) |
| *S. epidermidis* + Entada extract at 2.5% | 97 | 97 (+26%) | 94 (+92%) |

The results in Table 8 underline that under UV-B radiation, the extract of *Entada* seeds according to the invention is capable of protecting *Staphylococcus epidermidis*, the main bacterium component of the skin microbiome, from cell death.

The invention claimed is:

1. A process for producing an extract of seeds of the genus *Entada* enriched in entadamide A, comprising:
   (i) activating endogenous enzyme(s) by dispersion of the seeds under mechanical stirring in a seed/water weight ratio of about 0.02 to about 2;
   (ii) enzymatically hydrolyzing the dispersion obtained in step (i) by heat treatment at a temperature between about 25 and about 100° C. and for a time period of between about 2 minutes and about 12 hours, at a pH of between about 4 and about 8;
   (iii) inhibiting the enzymatic activity in the dispersion obtained in step (ii), the inhibition of said enzymatic activity comprising:
      a) adding an agent irreversibly inhibiting the activity of the endogenous enzymes in a volume ratio of inhibiting agent/water of between about 0.1 and about 10;
      b) heating the reaction medium obtained in step (iii/a) at a temperature of between about 25 and about 75° C. and for a time period of between about 2 minutes and about 12 hours;
      c) removing the inhibiting agent under reduced pressure to obtain an aqueous filtrate enriched in entadamide A and containing a native non-hydrolyzed phaseoloidin;
   (iv) adding a cosmetically acceptable solvent to the aqueous filtrate obtained in step (iii/c), then adjusting the pH between about 3 and about 7.

2. The process of claim 1, wherein the seeds are obtained from one or more of the species *Entada phaseoloides, Entada rheedei, Entada parvifolia, Entada pursaetha, Entada scandes, Entada gigas* and *Entada africana*.

3. The process of claim 1, wherein the seeds are obtained from the species *Entada phaseoloides*.

4. The process of claim 1, wherein the endogenous enzyme is a β-glucosidase.

5. The process of claim 1, wherein the extract comprises a weight content of between about 1 and about 5 mg/g of entadamide A, a weight content of between about 9 and about 85 mg/g of phaseoloidin, and traces of entadamide A glucone not exceeding a weight content of 0.2 mg/g.

6. The process of claim 1, wherein the extract comprises a phaseoloidin/entadamide A weight ratio between about 15 and about 25, and an entadamide A glucone/entadamide A weight ratio of less than 0.5.

7. The process of claim 1, wherein the pH during step (ii) is between about 4 and about 6.

8. The process of claim 1, wherein the inhibiting agent of step (iii/a) is an organic solvent miscible with water selected from the group consisting of glucose-added water and an alcohol.

9. The process of claim 8, wherein the alcohol is selected from the group consisting of ethanol, methanol, propanol and its isomers, butanol and its isomers, pentanol, hexanol, and mixtures thereof.

10. The process of claim 9, wherein the alcohol is ethanol.

11. The process of claim 1, wherein the cosmetically acceptable solvent of step (iv) is selected from the group consisting of 1,3-propanediol, 1,2-propanediol, methylpropanediol, phenoxypropanediol, 1,2-butanediol, 1,3-butanediol, 1,4-butane diol, 2,3-butanediol, 1,2-hexanediol, 1,2-dihydroxyethane, diethylene glycol, dipropylene glycol, triethylene glycol, tripropylene glycol, diethoxy diglycol, pentylene glycol, hexylene glycol, 1,2-octanediol, glycerin, and mixtures thereof.

12. The process of claim 11, wherein the cosmetically acceptable solvent is 1,3-propanediol.

13. A seed extract of the genus *Entada* enriched in entadamide A obtained by the process of claim 1, wherein the seed extract comprises a weight content of between about 1 and about 5 mg/g of entadamide A, a weight content of between about 9 and about 85 mg/g of phaseoloidin, and traces of entadamide A glucone not exceeding a weight content of 0.2 mg/g.

14. A composition which comprises a seed extract of the genus *Entada* enriched in entadamide A and one or more additives which are physiologically compatible with skin or appendages, wherein the amount of said extract is between 1% and 10% by weight relative to the total weight of the composition, wherein the seed extract is obtained by a process comprising:
   (i) activating endogenous enzyme(s) by dispersion of seeds of the genus *Entada* under mechanical stirring in a seed/water weight ratio of about 0.02 to about 2;
   (ii) enzymatically hydrolyzing the dispersion obtained in step (i) by heat treatment at a temperature between about 25 and about 100° C. and for a time period of between about 2 minutes and about 12 hours, at a pH of between about 4 and about 8;
   (iii) inhibiting the enzymatic activity in the dispersion obtained in step (ii), the inhibition of said enzymatic activity comprising:
      a) adding an agent irreversibly inhibiting the activity of the endogenous enzymes in a volume ratio of inhibiting agent/water of between about 0.1 and about 10;
      b) heating the reaction medium obtained in step (iii/a) at a temperature of between about 25 and about 75° C. and for a time period of between about 2 minutes and about 12 hours;
      c) removing the inhibiting agent under reduced pressure to obtain an aqueous filtrate enriched in entadamide A and containing a native non-hydrolyzed phaseoloidin,
   (iv) adding a cosmetically acceptable solvent to the aqueous filtrate obtained in step (iii/c), then adjusting the pH between about 3 and about 7, wherein the seed extract comprises a weight content of between about 1 and about 5 mg/g of entadamide A, a weight content of between about 9 and about 85 mg/g of phaseoloidin, and traces of entadamide A glucone not exceeding a weight content of 0.2 mg/g.

15. A method for preventing or combating the effects of solar radiation harmful to the skin, which comprises administering to a subject in need thereof a composition as defined in claim 14.

16. A method for preventing or combating skin signs resulting from atmospheric pollution, from contact with chemical xenobiotics or from smoky atmospheres, which comprises administering to a subject in need thereof a composition as defined in claim 14.

17. A method for maintaining the homeostasis of the microbiome present at the skin surface, which comprises administering to a subject in need thereof a composition as defined in claim 14.

18. A method for treating acne, seborrhea, rosacea or atopic dermatitis, which comprises administering to a subject in need thereof a composition as defined in claim 14.

19. The composition of claim 14, wherein the seeds are from one or more of the species *Entada phaseoloides, Entada rheedei, Entada parvifolia, Entada pursaetha, Entada scandes, Entada gigas* and *Entada africana*.

20. The composition of claim 19, wherein the seeds are from the species *Entada phaseoloides*.

21. The composition of claim 14, wherein the endogenous enzyme is a β-glucosidase.

22. The composition of claim 14, wherein the extract comprises a phaseoloidin/entadamide A weight ratio between about 15 and about 25, and an entadamide A glucone/entadamide A weight ratio of less than 0.5.

23. The composition of claim 14, wherein the pH during step (ii) is between about 4 and about 6.

24. The composition of claim 14, wherein the inhibiting agent of step (iii/a) is an organic solvent miscible with water selected from the group consisting of glucose-added water and an alcohol.

25. The composition of claim 24, wherein the alcohol is selected from the group consisting of ethanol, methanol, propanol and its isomers, butanol and its isomers, pentanol, hexanol, and mixtures thereof.

26. The composition of claim 25, wherein the alcohol is ethanol.

27. The composition of claim 14, wherein the cosmetically acceptable solvent of step (iv) is selected from the group consisting of 1,3-propanediol, 1,2-propanediol, methylpropanediol, phenoxypropanediol, 1,2-butanediol, 1,3-butanediol, 1,4-butanediol, 2,3-butanediol, 1,2-hexanediol, 1,2-dihydroxyethane, diethylene glycol, dipropylene glycol, triethylene glycol, tripropylene glycol, diethoxy diglycol, pentylene glycol, hexylene glycol, 1,2-octanediol, glycerin, and mixtures thereof.

28. The composition of claim 27, wherein the cosmetically acceptable solvent is 1,3-propanediol.

* * * * *